United States Patent [19]

Montero

[11] Patent Number: 4,544,358

[45] Date of Patent: Oct. 1, 1985

[54] DENTURE FIXTURES

[76] Inventor: Jose T. Montero, Andres Obispo, 37, Madrid-33, Spain

[21] Appl. No.: 595,862

[22] Filed: Apr. 2, 1984

[30] Foreign Application Priority Data

May 23, 1983 [ES]  Spain .................................... 272.396
Jan. 13, 1984 [ES]  Spain .................................... 276.825

[51] Int. Cl.⁴ ............................................. A61C 13/22
[52] U.S. Cl. .................................. 433/172; 433/178; 433/181
[58] Field of Search ............... 433/169, 170, 177, 178, 433/172

[56] References Cited

U.S. PATENT DOCUMENTS 3,990,150  11/1976  Giovannini .................... 433/177

Primary Examiner—Robert Peshock
Attorney, Agent, or Firm—Townsend and Townsend

[57] ABSTRACT

Denture fixture for connecting a denture to an existing tooth in a patient's mouth. The denture fixture includes an anchorage permanently joined to the denture and retention means mounted to a tooth and formed to interlock with anchoring means extending from the anchorage. The anchoring means includes two projecting stems arranged in an approximately horizontal plane. One stem has an enlarged end for mating with an aperture in the retention means; the other stem mates with a groove on one side of the retention means.

The apparatus has a low profile and is easily hidden from view. The denture is securely but flexibly positioned in the patient's mouth, is conveniently manufactured, and has no mechanism which can be obstructed by bits of food. The apparatus is not retained in position by forces exerted against the tooth and thus reduces wear on the tooth and the denture.

4 Claims, 5 Drawing Figures

DENTURE FIXTURES

The present invention deals with denture fixtures which allow the fixing or connection of dentures within the mouth of patients.

For the fixing or connection of dentures, for many years various sophisticated and complex mechanisms have been manufactured and called fixtures or 'ataches,' with the purpose of not having to use hooks on the natural or good teeth of the patient. These mechanisms have been placed on the non-visible parts of the mouth, for aesthetic reasons, and with the desired results as far as the front or external sections of the mouth are concerned, although not so in the occlusion or masticating sections. Ninety percent of cases have had to use metallic reinforcements, due to the greater height of the ataché, thus changing the natural form of the false teeth or denture.

The object of this invention is to obtain a fixture or atache which, due to its small size, allows the anchoring of dentures without any visible metal reinforcements, thus allowing the construction of false teeth of a natural color and which require no metallic reinforcements in the occlusion or masticating sector. The atache of the invention further allows loading large quantities of material on the male portion, given the new longitudinal-horizontal retention system that uses such a small space.

Furthermore, the invention atache further simplifies the laboratory technique. Given the format of the anchorage of the invention, future modifications in the dentrure may be effected without molesting the patient, without extra work for the dentist, all of which reduce labor costs.

The anchorage or fixture of the invention is composed of anchoring means which are permanently joined to, or solidary with, the denture, and retention means solidary with teeth immediately adjacent to the denture. The retention means is situated over the crest or top of the gums while the denture has, below it, within the adaptation channel of the gums, an enclosing section for coupling on said retention means.

The fixture or anchorage of the invention is characterized in that the mentioned retention means includes, starting from its upper surface, a central cylindrical apperture with an axis approximately parallel to the teeth of the denture and, either in its outer or inner surface, a longitudinal channel. The mentioned apperture opens laterally on the side opposite that where conexion to the denture is effected, and with a channel whose width is less than the diameter of said channel.

On the other hand, the anchoring means consist of, as per the invention, two small longitudinal bars or stems which are anchored to the denture. The mentioned bars or stems are situated along the lower housing of the denture which is coupled to the retention means.

One of the mentioned bars is disposed in a way that it couples with the channel of the retention means after elastically overriding the upper wall of said channel. This bar will preferably consist of a steel wire with a cross-section approximately equal to that of the retention means channel.

The other bar that forms part of the anchoring means has a diameter equal to, or slightly less than, the width of the opening of the circular apperture of the retention means. Furthermore, this second bar's tip ends in a sphere of a diameter approximately equal to that of the circular apperture of the retention means, so it may be coupled to same and form a ball-joint, thus serving as a conexion with freedom of movement for the unit.

The retention element, considering the size of natural teeth, is composed of a volumetrically small body, smaller than the size of the teeth and with different angles in order to later find proper basis and position in the acrylic or other material of the denture. Furthermore, the retention means may be coupled to any fixed or movable denture, or even to a natural tooth, being preferable manufactured from a metal normally utilized in dentures for later soldering to fixed or movable dentures.

The two small bars or stems which constitute the anchoring means may be connected to the acrylic or other deture material, or joined by solder to the traditional denture base or structure, which collaborate in the anchoring of the denture.

In order to clarify all the foregoing, following is a more detailed description of the denture fixture of the invention, with reference to the enclosed drawings, showing a preferred embodiment of the denture—which should not be taken as a limitation of the invention, but rather simply as an example of same.

Figure 2:
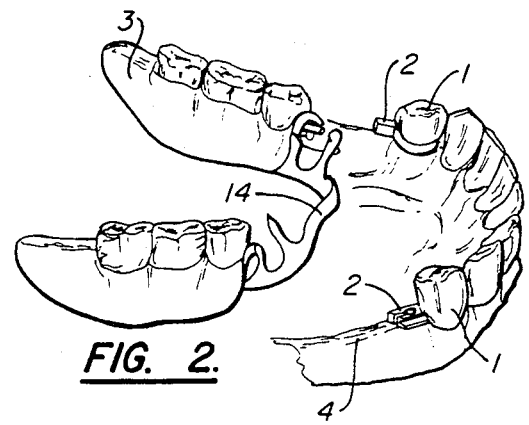
FIG. 2 is a perspective view of a lower maxiliary and a denture constructed as per this invention, shown at a coupling stage.
Figure 3:
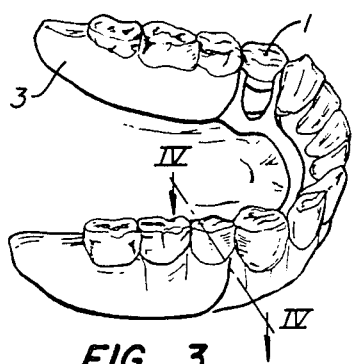
FIG. 3 is a view, similar to that of FIG. 2, showing the denture already coupled.
Figure 4:
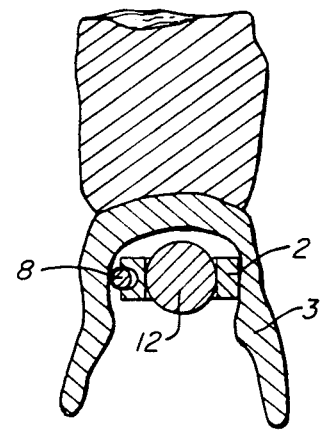
FIG. 4 is an enlarged view of a section of FIG. 3, cut along line IV—IV.

In the embodiment shown in FIGS. 2 and 3, the lower maxilliary only carries the incisors, canine and first molar teeth, numbered 1. Each of the molars carries, connected to it, a retention means referenced 2.

The retention means 2 is composed of a metallic part, duly formed as required, small, which anchores on the molar teeth adjacent that section where the denture 3 is to be located. The retention means 2 runs along the top of gums 4.

Figure 1:
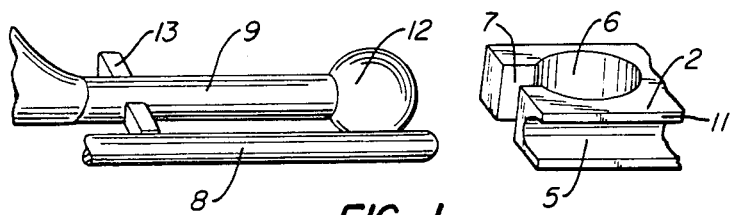
FIG. 1 is a perspective view of the retention section as well as anchoring means which form part of the denture.

As may be better appreciated in FIG. 1, retention means 2 has, on its outer face, a longitudinal channel 5. Said channel could also be on the opposite face. Furthermore, the retention means, as of its upper face, shows a cylindrical vertical aperture 6 which opens towards the outside on the side opposite that where the denture 1 is to be anchored, by means of the channel 7 and of a width smaller than that of the diameter of aperture 6, thus defining a narrowing section of said opening.

On the other hand, the anchoring means connected to the denture 3 are composed of two small bars or stems referenced 8 and 9 in FIG. 1.

Figure 5:
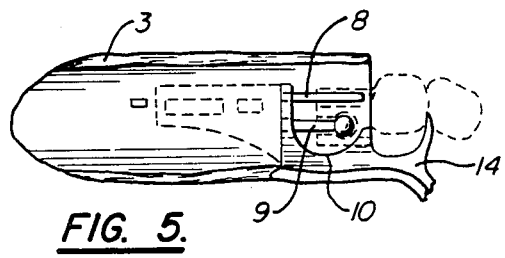
FIG. 5 is a top view of one of the sides of the denture under consideration.

As may be seen in FIG. 5, the bars 8 and 9 are anchored at their lower part on denture 3, on a longitudinal manner, and on cantilever from the structural sector 10 destined to be coupled to the retention means 2. Small bar 8 could consist of a steel wire with a cross-section approximately equal to that of channel 5 and place in such a way as to rest against the upper wall 11 of channel 5 when coupling denture 3, having to undergo elastic deformation to go over said wall and couple or connect with mentioned channel 5.

Small bar or stem 9, on the other hand, shall have a cylindrical configuration, of a diameter equal to or slightly smaller than the width of channel 7 in FIG. 1. This bar 9 additionally has its free end formed as an enlarged cylinder with a diameter approximately equal to that of the cylindrical aperture 6. Bar 9 is placed in such a way as to have its enlarged cylindrical section 12 located within the cylindrical aperture 6 of the retention means 2 upon coupling denture 3 over the gums.

With this structure, denture 3 is fixed to retention means 2 by means of small bar or stem 8 and bar or stem 9 with its sphere 12 which acts as a joint.

Bars 8 and 9 may be anchored to the acrylic material of denture 3, hence having to carry an enlarged sector or side projections 13 which facilitate its execution and impede any accidental rotation. These mentioned small bars or stems may also be soldered to traditional sections 14, base of the denture, which is normally made of a metal.

As may be understood, denture 3 may have any configuration or form, depending on the space or spaces they are to cover in the upper or lower gums, on both sides, or on only one of said gums.

Tooth 1, on which retention means 2 is to be connected, can consist of a natural tooth or a mobile or fixed denture.

I claim:

1. A denture fixture for positioning and stabilizing a denture to a tooth, the tooth being adjacent the denture and embedded in gums and having a substantially upright tooth axis, the denture fixture comprising:

anchoring means affixed to the denture and having first and second stems resiliently extending from the denture toward the tooth, the first stem including a reduced diameter section and an enlarged portion spaced apart from the denture, and the second stem being in parallel, spaced apart relationship to the first stem and lying in a substantially horizontal plane which includes the first stem; and retention means mounted to the tooth in the region of the gums and extending toward the denture over the gums to a retention means end, the retention means having:

a substantially cylindrical aperture for receiving the enlarged portion of the first stem, the cylindrical aperture being aligned approximately parallel to the tooth, a first channel extending between the aperture and the retention means end and being formed to receive a section of the first stem located between the enlarged portion and the denture, and a longitudinal second channel substantially parallel to and spaced apart from the first channel for receiving a portion of the second stem.

2. The denture fixture of claim 1, wherein the second channel is formed to be a generally cylindrical groove in a side of the retention means adjacent a vestibular portion of the tooth, and wherein the retention means has a height along an axis parallel to the tooth axis that is substantially less than a corresponding height of the tooth.

3. The denture fixture of claim 1 wherein the first stem includes a steel wire having a circular cross-section, and wherein the first channel has a width that is substantially equal to the diameter of the steel wire.

4. The denture fixture of claim 1 wherein the enlarged portion of the first stem is generally spherical, wherein a diameter of the enlarged portion is slightly less than a diameter of the cylindrical aperture, and wherein the width of the reduced diameter section is slightly less than the width of the first channel.

* * * * *